US009506846B2

(12) United States Patent
Rubner et al.

(10) Patent No.: US 9,506,846 B2
(45) Date of Patent: Nov. 29, 2016

(54) HIGH DEFINITION NANOMATERIALS

(71) Applicant: Massachusetts Institute of Technology, Cambridge, MA (US)

(72) Inventors: Michael Rubner, Westford, MA (US); Brian L. Wardle, Lexington, MA (US); Robert E. Cohen, Jamaica Plain, MA (US); Mehmet Toner, Wellesley, MA (US); Fabio Fachin, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 13/962,202

(22) Filed: Aug. 8, 2013

(65) Prior Publication Data

US 2014/0079601 A1  Mar. 20, 2014

Related U.S. Application Data

(60) Provisional application No. 61/680,770, filed on Aug. 8, 2012.

(51) Int. Cl.

| | |
|---|---|
| *G01N 15/06* | (2006.01) |
| *G01N 33/00* | (2006.01) |
| *G01N 33/48* | (2006.01) |
| *B01L 3/00* | (2006.01) |
| *G01N 35/00* | (2006.01) |
| *G01N 1/10* | (2006.01) |
| *G01N 1/34* | (2006.01) |
| *G01N 1/40* | (2006.01) |

(52) U.S. Cl.
CPC ............ *G01N 1/34* (2013.01); *B01L 3/502707* (2013.01); *B01L 3/502753* (2013.01); *B01L 2300/0636* (2013.01); *B01L 2300/0877* (2013.01); *B01L 2300/0896* (2013.01); *B01L 2400/086* (2013.01); *G01N 2001/4088* (2013.01)

(58) Field of Classification Search
CPC ...... G01N 15/06; G01N 33/00; G01N 33/48; G01N 3/00; G01N 35/00; G01N 1/10; B01L 3/00
USPC ................ 422/68.1, 502, 503; 436/43, 180; 977/700, 707, 712, 701, 773
See application file for complete search history.

(56) References Cited

U.S. PATENT DOCUMENTS

| | | | |
|---|---|---|---|
| 8,075,863 B2 * | 12/2011 | Hart et al. | ................. 423/447.3 |
| 2006/0032329 A1 * | 2/2006 | Rubinstein et al. | ............ 75/255 |
| 2006/0065528 A1 * | 3/2006 | Lopez et al. | .................. 204/450 |

FOREIGN PATENT DOCUMENTS

WO  WO 2012/016136  2/2012

OTHER PUBLICATIONS

Kim, Jun Young, et al., Chemistry of Materials "Formation of Nanoparticle-Containing Multilayers in Nanochannels via Layer-by-Layer Assembly," Nov. 8, 2010,vol. 22, No. 33, pp. 6409-6415.
International Preliminary Report on Patentability from PCT/US2013/054092 mailed Feb. 19, 2015.
International Search Report and Written Opinion from PCT/US2013/054092 mailed Jan. 17, 2014.

\* cited by examiner

*Primary Examiner* — Brian J Sines
(74) *Attorney, Agent, or Firm* — Steptoe & Johnson LLP

(57) ABSTRACT

A microfluidic device for manipulating particles can include a substrate and one or more obstacles, each obstacle comprising a plurality of aligned nanostructures including a plurality of nanoparticles or a plurality of polymer layers, or a combination thereof. The obstacle on a substrate can be forests with intra-carbon nanotube spacing ranging between 5-100 nm for isolation of particles such as very small viruses and proteins.

6 Claims, 16 Drawing Sheets

HIGH DEFINITION NANOMATERIALS

CLAIM OF PRIORITY

This application claims the benefit of prior U.S. Provisional Application No. 61/680,770, filed on Aug. 8, 2012, which is incorporated by reference in its entirety.

STATEMENT OF GOVERNMENT SUPPORT

This invention was made with government support under Grant No. DMR0819762 awarded by the National Science Foundation. The government has certain rights in the invention.

TECHNICAL FIELD

The present invention relates to manipulation of particles, e.g., biological particles, and more particularly to fluidic capture, separation, and concentration or enrichment of particles.

BACKGROUND

Most clinical diagnostics and basic research studies aimed at understanding the causes underlying disease require isolation of specific biomolecules or cells from complex samples such as blood, saliva, and cell culture supernatant. Sometimes such bioparticles of interest are present in the samples in very small quantities. This is the case, for example, of antigen-specific T-cells, circulating tumor cells, and HIV viral particles, which can be used, for example, for monitoring immune responses, cancer, and AIDS progression respectively.

Fluidic (macroscopic) and microfluidic devices can be used for detecting, capturing, separating, and enriching particles of many types that are suspended or dispersed in a fluid. In some cases, microfluidic devices include obstacles coated with binding moieties that selectively bind to specific bioparticles that contact surfaces of the obstacle. In some situations, the obstacles are formed from solid materials such as silicon, polymers, and glass. Such materials possess attributes including geometrical definability (e.g., using photolithography), and compatibility with both gas and liquid-phase chemical functionalization processes. Geometrical definability, e.g., in microfluidic applications, allows control of the fluid dynamics inside the channels. Selective functionalization of the structural features allows isolation and manipulation of specific particles. In addition, some of the materials, such as polydimethylsiloxane (PDMS), exhibit optical transparency, which allows on-line visual monitoring of the tests and simplifies bio-assay readout designs.

However, in such prior devices, fluid-boundary interactions at the surface of obstacles in the fluid path can have detrimental effects on the desired functions of these devices.

SUMMARY

In general, a fluidic device for manipulating particles can include a substrate that defines a fluid path and one or more obstacles, each obstacle comprising a plurality of aligned nanostructures, wherein adjacent nanostructures form an obstacle outer surface that occupies a defined space in the fluid path; wherein the one or more obstacles are fixedly arranged within the fluid path such that some expected paths within the fluid path pass around the obstacle outer surface and some expected paths within the fluid path pass through the obstacle outer surface and into a network of spaces within the obstacle between the nanostructures, and wherein the nanostructures within the obstacles alter a flow field near the obstacle outer surface compared to obstacles of the same defined space made of a material through which fluid does not flow.

A method of manufacturing a fluid device can comprise growing a plurality of nanostructures on a substrate, and depositing a plurality of nanoparticles or a plurality of polymer layers, or a combination thereof on the substrate including nanostructures.

The nanostructures can include a plurality of nanoparticles, a plurality of polymer layers, or a combination thereof. The nanostructure can be a carbon nanotube.

The obstacle on a substrate can be forests with intra-carbon nanotube spacing ranging between 5-100 nm for isolation of particles such as very small viruses and proteins.

Other aspects, embodiments, and features will be apparent from the following description, the drawings, and the claims.

BRIEF DESCRIPTION OF THE DRAWINGS

FIGS. 5A and 5C are close-ups of FIG. 5B, in varying degrees.

DETAILED DESCRIPTION

Figure 1:
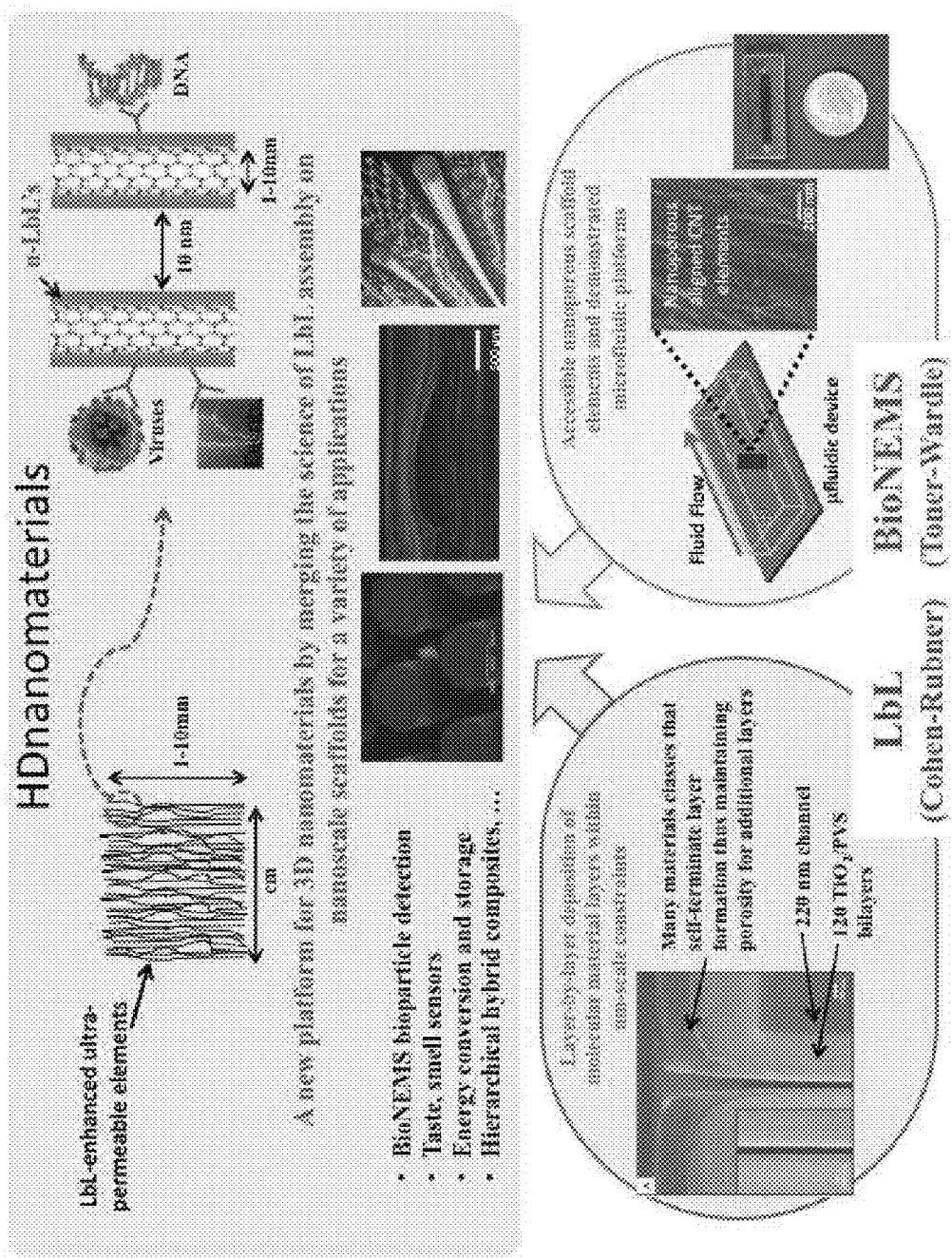
FIG. 1 is a schematic depicting Cohen-Rubner's layer-by-layer (LBL) work with Toner-Wardle's nanoporous elements in microfluidics to yield a new platform for understanding LBL in 3 dimensions.

Synthetic superhydrophobic surfaces have been fabricated through various approaches. A superhydrophobic surface is a surface that has a water droplet advancing contact angle of 150° or higher and the receding contact angle is within 5° of the advancing contact angle. Previous methods of fabricating superhydrophobic coatings can be expensive, substrate limited, require the use of harsh chemical treatments, or cannot be easily scaled-up to create large-area uniform coatings. Consequently, many of these methods are not readily suitable for the coating of the surfaces of complex substrates like the channels of a microfluidic device, fiber surfaces, or intricate shapes, such as, for example, found on a stent.

A superhydrophobic surface can be fabricated from a polyelectrolyte coating. A polyelectrolyte has a backbone with a plurality of charged functional groups attached to the backbone. A polyelectrolyte can be polycationic or polyanionic. A polycation has a backbone with a plurality of positively charged functional groups attached to the backbone, for example poly(allylamine hydrochloride). A polyanion has a backbone with a plurality of negatively charged functional groups attached to the backbone, such as sulfonated polystyrene (SPS) or poly(acrylic acid), or a salt thereof. Some polyelectrolytes can lose their charge (i.e., become electrically neutral) depending on conditions such as pH. Some polyelectrolytes, such as copolymers, can include both polycationic segments and polyanionic segments.

Layer-by-layer processing of polyelectrolyte multilayers can be utilized to fabricate conformal thin film coatings with molecular level control over film thickness and chemistry. Charged polyelectrolytes can be assembled in a layer-by-layer fashion. In other words, positively- and negatively-charged polyelectrolytes can be alternately deposited on a substrate. One method of depositing the polyelectrolytes is to contact the substrate with an aqueous solution of polyelectrolyte at an appropriate pH. The pH can be chosen such that the polyelectrolyte is partially or weakly charged. The multilayer can be described by the number of bilayers it includes, a bilayer being the structure formed by the ordered application of oppositely charged polyelectrolytes. For example, a multilayer having the structure PAH-PAA-PAH-PAA-PAH-PAA would be said to be made of three bilayers.

Multilayer thin films containing nanoparticles of $SiO_2$ can be prepared via layer-by-layer assembly (see Lvov, Y.; Ariga, K.; Onda, M.; Ichinose, I.; Kunitake, T. *Langmuir* 1997, 13, (23), 6195-6203, which is incorporated by reference in its entirety). Other studies describe multilayer assembly of $TiO_2$ nanoparticles, $SiO_2$ sol particles and single or double layer nanoparticle-based anti-reflection coatings. See, for example, Zhang, X-T.; et al. *Chem. Mater.* 2005, 17, 696; Rouse, J. H.; Ferguson, G. S. *J. Am. Chem. Soc.* 2003, 125, 15529; Sennerfors, T.; et al. *Langmuir* 2002, 18, 6410; Bogdanvic, G.; et al. *J. Colloids Interface Science* 2002, 255, 44; Hattori, H. *Adv. Mater.* 2001, 13, 51; Koo, H. Y.; et al. *Adv. Mater.* 2004, 16, 274; and Ahn, J. S.; Hammond, P. T.; Rubner, M. F.; Lee, I. *Colloids and Surfaces A: Physicochem. Eng. Aspects* 2005, 259, 45, each of which is incorporated by reference in its entirety. Incorporation of $TiO_2$ nanoparticles into a multilayer thin film can improve the stability of the superhydrophilic state induced by light activation. See, e.g., Kommireddy, D. S.; et al. *J. Nanosci. Nanotechnol.* 2005, 5, 1081, which is incorporated by reference in its entirety.

Nanoparticles can be applied to the multilayer, to provide a nanometer-scale texture or roughness to the surface. The nanoparticles can be nanospheres such as, for example, silica nanospheres, titania nanospheres, polymer nanospheres (such as polystyrene nanospheres), or metallic nanospheres. The nanoparticles can be metallic nanoparticles, such as gold or silver nanoparticles. The nanoparticles can have diameters of, for example, between 1 and 1000 nanometers, between 10 and 500 nanometers, between 20 and 100 nanometers, or between 1 and 100 nanometers. A nanoparticle can be a carbon-based nanostructure. A carbon-based nanostructure is a nanostructure that comprises at least 30% carbon by mass. In some embodiments, the carbon-based nanostructures may comprise at least about 40%, at least about 50%, at least about 60%, at least about 70%, at least about 80%, at least about 90%, or at least about 95% of carbon by mass, or more. Examples of carbon-based nanostructures include carbon nanotubes, carbon nanowires, carbon nanofibers, and the like.

The particles, e.g., biological particles, of different cross-sectional dimensions suspended in a fluid sample are flowed through the fluid path formed in a device, e.g., a microfluidic device. A porous array of obstacles, where each obstacle is formed of multiple aligned nanostructures that render the obstacle substantially porous, are arranged and fixed within the fluid path formed in the device to capture, separate, concentrate, and enrich particles by either mechanically capturing the particles or chemically binding the particles or both. A microfluidic device can include a substrate that defines a fluid path and one or more obstacles, each obstacle comprising a plurality of aligned nanostructures and having an outer boundary of an obstacle in the fluid path. In some embodiments, the one or more obstacles are fixedly arranged within the fluid path such that some expected paths within the fluid path pass through the outer surface of an obstacle and some expected paths within the fluid path pass through the outer surface of an obstacle and into a network of spaces within the obstacle between the nanostructures, and wherein the nanostructures within the obstacles alter a flow field near the outer surface of the obstacle compared to obstacles of the same defined space made of a material through which fluid does not flow.

HDnanomaterials are a new class of 3D bulk material elements that can be tailored at the sub nm-scale by combining solution-based layer-by-layer (LBL) processing and related techniques with the bulk nanoporous carbon scaffolds recently developed and demonstrated as microfluidic elements. A broad palette of LBL multilayer coating techniques in aqueous solution focusing on layer assembly (sub-nm thick layers) inside spaces approaching 10's of nm has been developed (see FIG. 1). Also, microfluidic devices integrating ultra-high porosity (>99% porosity) nanoporous bulk elements have been recently demonstrated for flow-field manipulation and filtering of nm- through micro-scale bioparticles.

Figure 11:
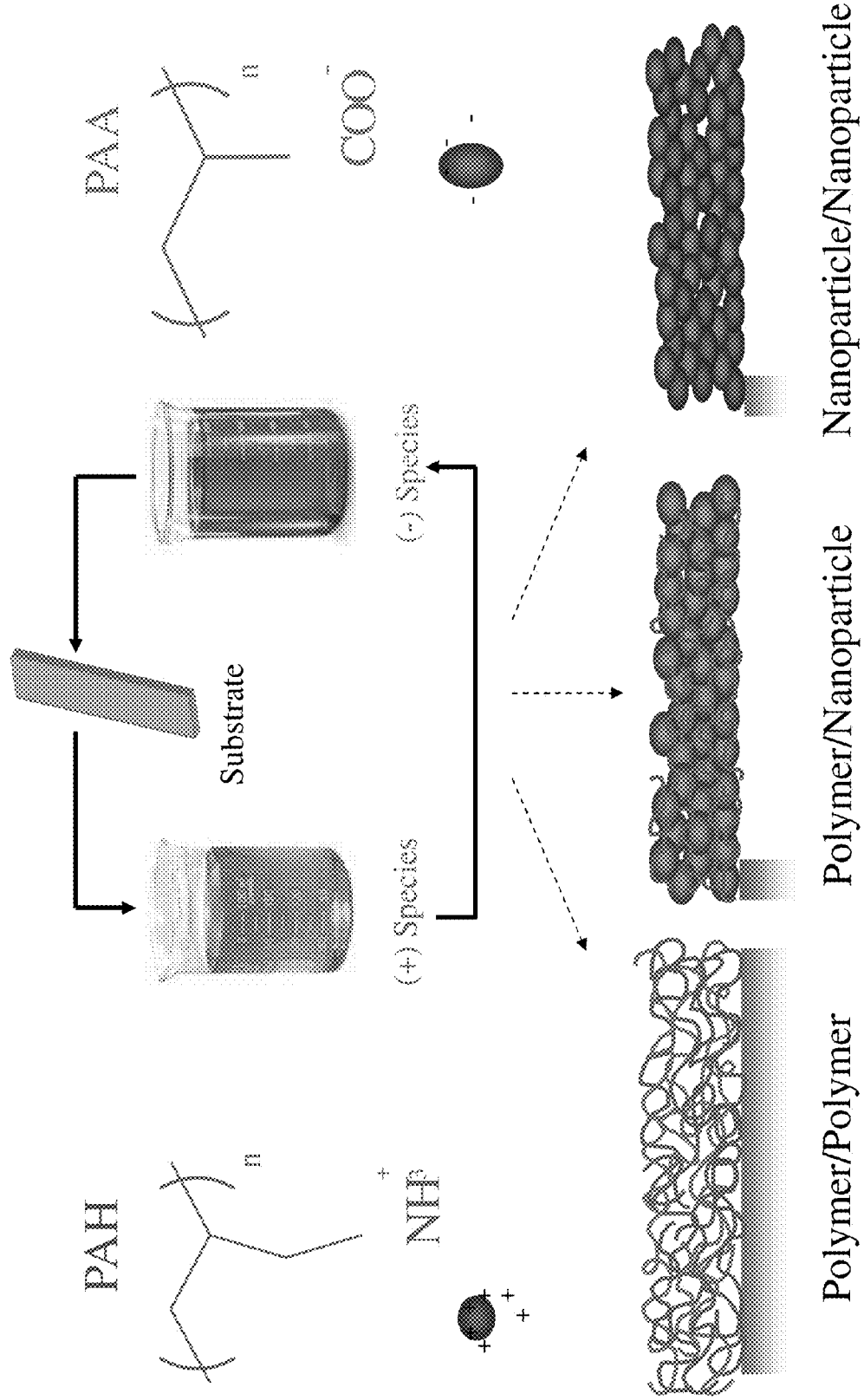
FIG. 11 is a schematic of LBL assembly technique.
Figure 12:
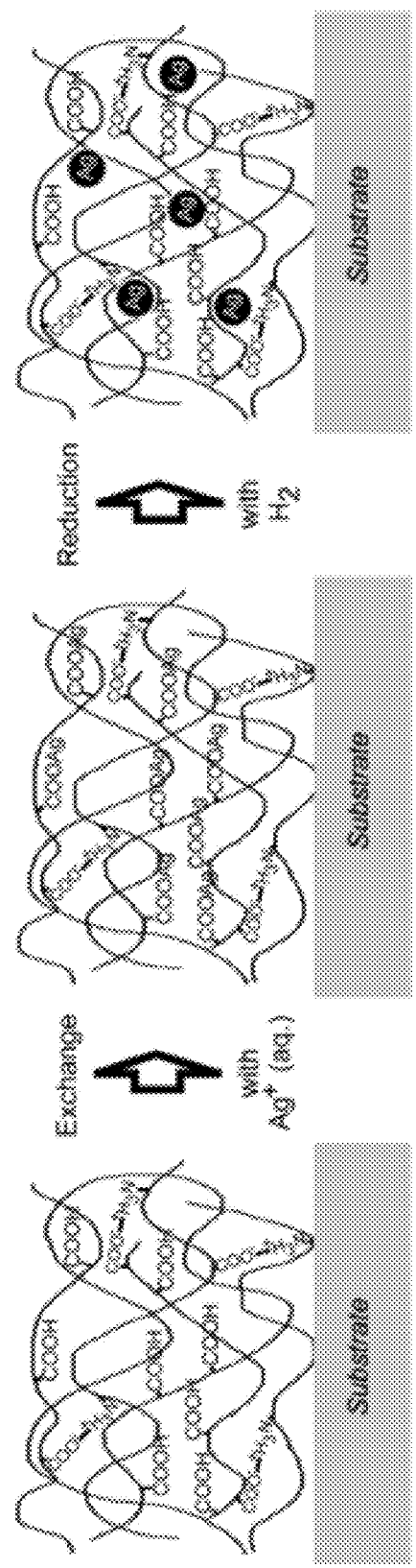
FIG. 12 is a schematic of an LBL example of nanoparticles and polymer layers.

The nanoporous microfluidic elements provide a textured 3D set of nano-scale surfaces that are uniquely accessible to the LBL technique due to their ultrapermeable nature (measured Darcy drag coefficient 5 orders of magnitude lower than any reported), going far beyond what is capable with nanoscale filtering concepts. FIG. 11 shows a schematic of LBL assembly technique. The assembly conditions can be used to control nano- and microscale texture, porosity, chemical functionalization, mechanical properties, cell attachment and resistance. FIG. 12 shows a schematic of an LBL example of nanoparticles and polymer layers. A platform for creating 3D bulk materials where self-terminating molecular layers are assembled on macroscopic (cm-scale) nanoporous scaffolds with the possibility of spatial tailoring in all 3 dimensions is disclosed. Developing fundamental understanding of LBL assembly onto the 3D nanoporous elements, extending the recent space-constrained LBL work to smaller spaces (accessible via aqueous routes) approaching single nm dimensions, while simultaneously extending it from planar facing channels to 3D bulk nanoscale features, i.e., for an equivalent volume of channel makes it possible for the LBL to occur on 3D surfaces with 5-20× smaller constraint, and >2000% higher surface area. BioNEMS devices for bioparticle isolation will directly benefit from the LBL as it will allow a myriad of new functionalities for the devices to be targeted, moving away from simply functionalizing to truly tailoring, and enabling new types of bioparticle manipulation; a targeted device effort will show LBL-enabled bioparticle capture and manipulation focusing on the HIV virus, ~100 nm in size and currently inaccessible by state-of-the-art N/MEMS platforms. Success in that device will lead to much broader investigations of nanoparticle-based information about disease processes in the body in future work, including enabling investigations of before-untargeted information packets in fluids (e.g., blood contains nm-scale exosomes in small quantities that could be used to track disease evolution and treatment effectiveness). This work on LBL into bulk nanoporous elements will impact numerous other fields such as filtration, titration, nanostructured anodes/cathodes etc.

The ability to tailor interfaces has led to many of the technological advances in materials in recent decades across all domains and is particularly relevant when considering nanoscale effects. See Thomas P. Burg, Michel Godin, Scott M. Knudsen, Wenjiang Shen, Greg Carlson, John S. Foster, Ken Babcock and Scott R. Manalis, *Nature* 446, 1066-1069 (26 Apr. 2007), Hakho Lee, Eric Sun, Donhee Ham and Ralph Weissleder, *Nature Medicine* 14, 869-874 (2008), Deirdre R. Meldrum and Mark R. Holl, *Science* 16 Aug. 2002: 297 (5584), 1197-1198, George M. Whitesides, *Nature* 442, 368-373 (27 Jul. 2006), Todd M. Squires, Robert J. Messinger and Scott R. Manalis, *Nature Biotechnology* 26, 417-426 (2008), and Fernando Patolsky, Gengfeng Zheng, Oliver Hayden, Melike Lakadamyali, Xiaowei Zhuang, and Charles M. Lieber, *PNAS* 2004 101 (39), 14017-14022, each of which is incorporated by reference in its entirety.

Figure 2A:
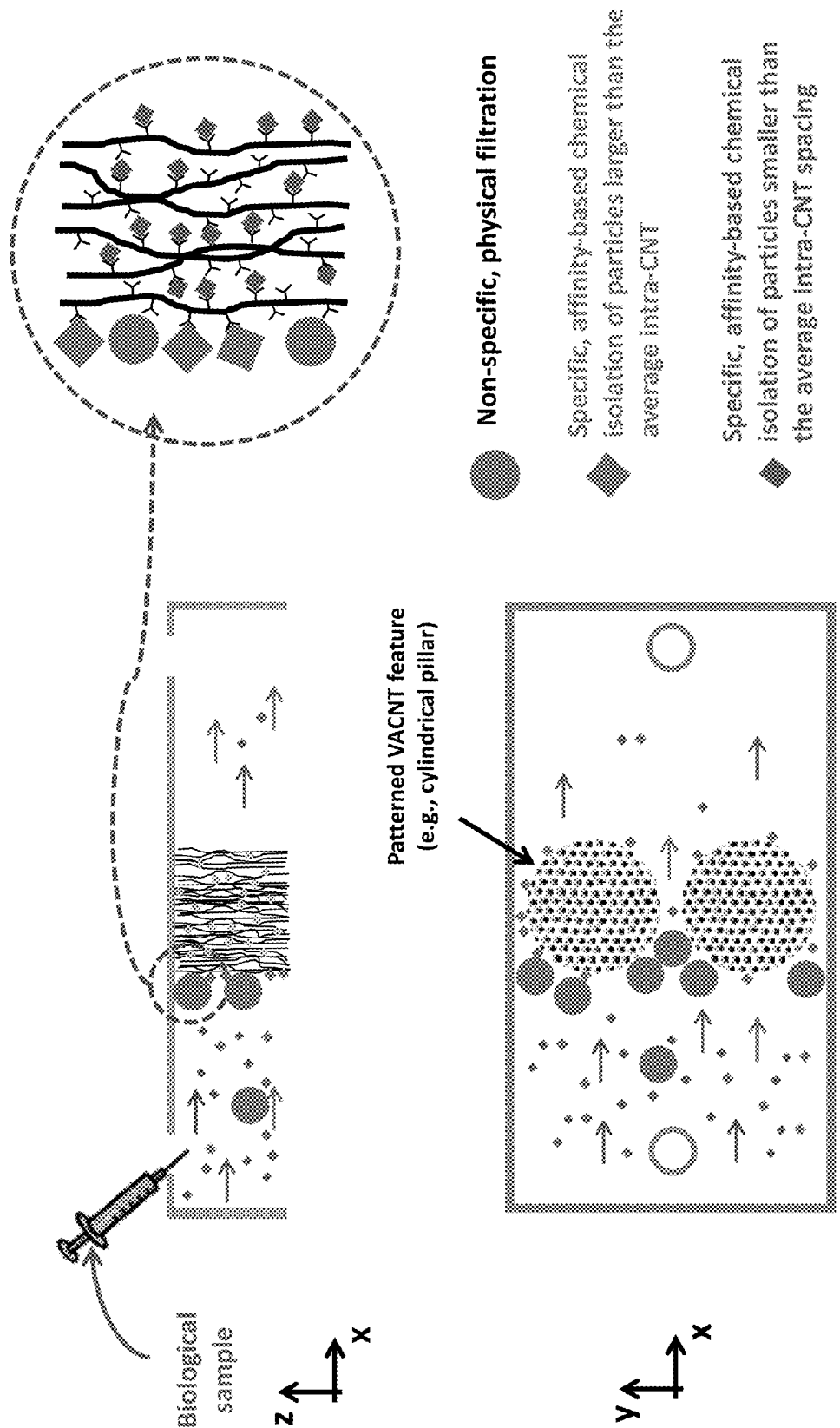
FIG. 2A is a schematic depicting characteristics of nanoporous elements in aqueous solution (fluid flow) and operation of one microfluidic bioparticle isolation scheme.
Figure 2C:
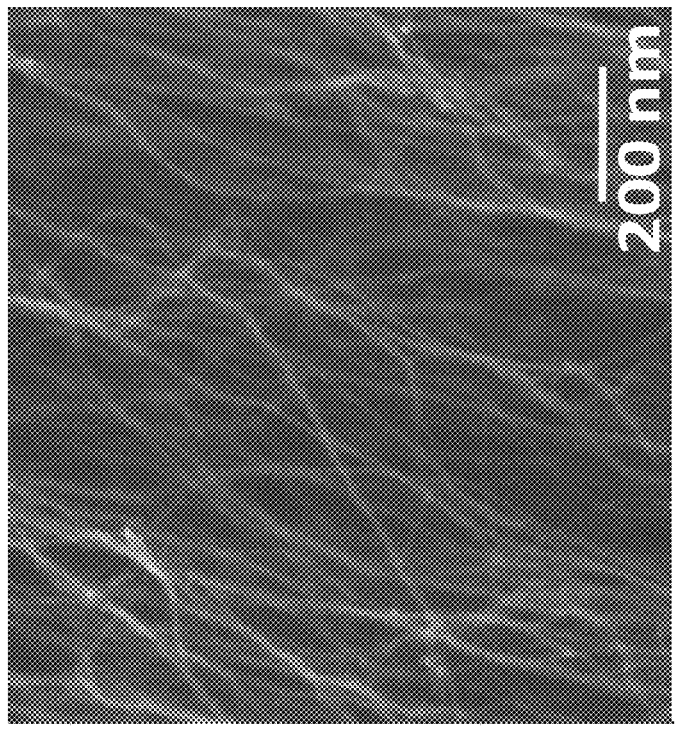
FIG. 2C is an image depicting the vertical alignment of an example.
Figure 2B:
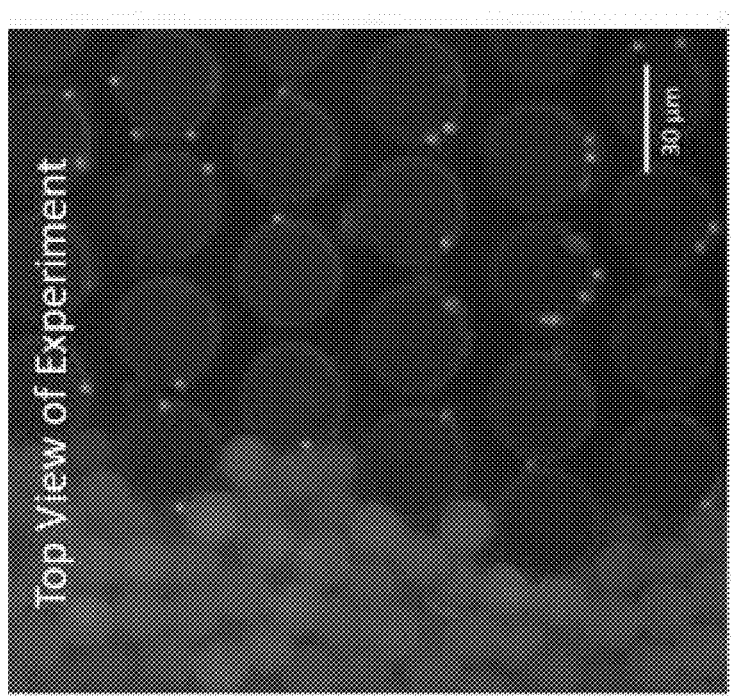
FIG. 2B is an image depicting the top view of an example.

Biomedical research has particularly benefited from advances in surface chemistry and surface manipulation, enabling a large number of applications from controllable release/adsorption of proteins to affinity chromatography. See Thomas P. Burg, Michel Godin, Scott M. Knudsen, Wenjiang Shen, Greg Carlson, John S. Foster, Ken Babcock and Scott R. Manalis, *Nature* 446, 1066-1069 (26 Apr. 2007), M. P. MacDonald, G. C. Spalding and K. Dholakia, *Nature* 426, 421-424 (27 Nov. 2003), John A. Davis, David W. Inglis, Keith J. Morton, David A. Lawrence, Lotien R. Huang, Stephen Y. Chou, James C. Sturm and Robert H. Austin, *PNAS* 2006 103 (40) 14779-14784, Anne Y. Fu, Charles Spence, Axel Scherer, Frances H. Arnold and Stephen R. Quake, *Nature Biotechnology* 17(11):1109-1111, Todd M. Squires, Robert J. Messinger and Scott R. Manalis, *Nature Biotechnology* 26, 417-426 (2008), Sunitha Nagrath, Lecia V. Sequist, Shyamala Maheswaran, Daphne W. Bell, Daniel Irimia, Lindsey Ulkus, Matthew R. Smith, Eunice L. Kwak, Subba Digumarthy, Alona Muzikansky, Paula Ryan, Ulysses J. Balis, Ronald G. Tompkins, Daniel A. Haber & Mehmet Toner, *Nature* 450, 1235-1239 (20 Dec. 2007), and Dale L. Huber, Ronald P. Manginell, Michael A. Samara, Byung-Il Kim, Bruce C. Bunker, *Science* 18 Jul. 2003: 301 (5631) 352-354, each of which is incorporated by reference in its entirety. Layer-by-layer deposition has emerged as a facile and flexible route towards layered molecular assembly, unlocking great potential particularly on films and surfaces. See, Fernando C. Vasconcellos, Albert J. Swiston, Marisa M. Beppu, Robert E. Cohen, Michael F. Rubner, *Biomacromolecules* 2010 11 (9), 2407-2414, Jonathan P. DeRocher, Pan Mao, Jongyoon Han, Michael F. Rubner, Robert E. Cohen, *Macromolecules* 2010 43 (5), 2430-2437, Daeyeon Lee, Michael F. Rubner, and, Robert E. Cohen, *Nano Letters* 2006 6 (10), 2305-2312 , Jun Young Kim, Jonathan P. DeRocher, Pan Mao, Jongyoon Han, Robert E. Cohen, Michael F. Rubner, *Chemistry of Materials* 2010 22 (23), 6409-6415, and Khek-Khiang Chia, Michael F. Rubner, Robert E. Cohen, *Langmuir* 2009 25 (24), 14044-14052, each of which is incorporated by reference in its entirety. However, extending LBL techniques to bulk materials with controlled morphology is largely an unexplored area. Disclosed herein is a platform based on microfluidics for achieving 3D LBL via solution-processing into nanoporous scaffolds. Materials having scale of mm in height and cm in length and width, but is extensible to meter-scale bulk materials in creating bulk nanostructured composite materials for aerospace and infrastructure applications are employed. The LBL chemistries are quite broad and have been used to manipulate many materials classes, from synthetic and biological macromolecules to ceramic and metallic nanoparticles. The technical risk is quite low that the nanoporous elements are accessible via aqueous solutions in their microfluidic bioNEMS devices (FIG. 2), and Cohen-Rubner have a broad palette of materials that can be placed and tuned via solution-based LBL. See, Sunitha Nagrath, Lecia V. Sequist, Shyamala Maheswaran, Daphne W. Bell, Daniel Irimia, Lindsey Ulkus, Matthew R. Smith, Eunice L. Kwak, Subba Digumarthy, Alona Muzikansky, Paula Ryan, Ulysses J. Balis, Ronald G. Tompkins, Daniel A. Haber & Mehmet Toner, *Nature* 450, 1235-1239 (20 Dec. 2007), and F. Fachin, G. D. Chen, M. Toner, and B. L. Wardle, *Proceedings of IEEE Sensors* 2010, 47-51, 2010, each of which is incorporated by reference in its entirety. The scientific impact is in understanding (and potentially breaking through) any nm-scale constraint limitations of LBL in 3 dimensions, and the technological impact is extremely broad since applications for such tailored materials abound: on-chip bioparticle (100 nm HIV virus targeted due to global health needs) manipulation will be demonstrated opening new possibilities in diagnosis and monitoring by pushing down into before-unexplored lengthscales of particles. Application areas from energy-storage and conversion materials to high-throughput taste and smell sensors will also be enabled. FIG. 2A shows characteristics of nanoporous elements in aqueous solution (fluid flow) and operation of one microfluidic bioparticle isolation scheme. FIGS. 2B-2C show 99% of porosity and 80 nm intra-carbon nanotube spacing. These techniques form a platform for LBL studies as well as enabling new capabilities (devices targeting HIV diagnosis).

Disclosed herein is a method to create functional 3D molecular-layered materials (HDnanomaterials) via LBL onto ultra-high porosity scaffolds with nm-scale spacing and width (see FIG. 1). The work is primarily experimentally based, and significantly extends recent space-constrained LBL work by utilizing the novel nanoporous microfluidic platform. The nm-scale scaffolds in the platform are aligned carbon nanotube (CNT) forests that have been developed as a new element in bulk composite materials, and recently integrated into microfluidics for bioparticle separation and isolation. Thus, molecular assembly in 3D on high-permeability nanoscale (and spaced) carbon nanotube scaffolds is possible through solution-processing. Key to success of the work is combining the ultra-high permeability (UHP) of the nanoporous elements, which allows all the surface of the elements to be accessed through solution processing, while the self-terminating LBL chemistries that will maintain the unique ultra-high permeability through multiple layer depositions. This attribute has two major implications for this work: (i) LBL assembly can occur into the carbon nanotube forests and the process can be repeated 10's to 100's of times while maintaining the needed ultra-high permeability, and (ii) the resulting nanoporous features with LBL-functionality can be utilized directly in microfluidics (fluids and gases will still permeate at high fluxes), or as post-processible elements for making 3D tailored materials, e.g., nanocomposites can be realized by capillary-assisted polymer infiltration following the extensive work of Wardle's group (see, E J García, A J Hart, B L Wardle and A H Slocum, 2007 *Nanotechnology* 18 165602, which is incorporated by reference in its entirety), including for bulk macro materials (see, Wicks, S. S., Guzmán de Villoria, R., and B. L. Wardle, "Interlaminar and Intralaminar Reinforcement of Composite Laminates with Aligned Carbon Nanotubes," *Composites Science and Technology*, 70 (2010), pp. 20-28, which is incorporated by reference in its entirety).

The origin of the ultra-high permeability begins with the classical treatment of fluid flow through porous materials as described by the Darcy-Forchheimer law (see, S. L. Lee and J. H. Yang, *International Journal of Heat and Mass Transfer* 40 (13), September 1997, 3149-3155, and Namgyun Jeong et al 2006 *J. Micromech. Microeng.* 16 2240, each of which is incorporated by reference in its entirety):

$$\frac{\Delta P}{L}\frac{D^2}{\mu \bar{u}} = \frac{D^2}{\kappa} + FRe_D$$

where $\Delta P$ is the pressure drop across the channel per unit dimension x, L is the channel length, D and $\kappa$ are the average diameter and the fluid permeability of the porous features, u and $\mu$ are the fluid velocity and dynamic viscosity, $Re_D$ is the Reynolds number (based on average feature diameter—D), and F is the Forchheimer coefficient. The dimensionless terms $D^2/\kappa$, $FRe_D$, and their sum are typically referred to as the Darcy drag, the Forchheimer drag and the Darcy-Forchheimer drag, respectively. At the low Reynolds regimes typical of microfluidic devices, the Forchheimer drag is negligible while Darcy drag becomes the primary performance index. Highly fluid-accessible materials are therefore characterized by very low Darcy drag values, as this yields minimum pressure drop across the channel. Darcy drag is highly scale dependent, favoring designs with small features and high porosity. Integration of nanoporous elements in microfluidic channels is therefore particularly attractive, as their extremely small feature size could yield very small values of Darcy drag. High values of Darcy drag are what impairs the ability of all nanoscale filtering concepts to process particles in fluids: the flow rates are extremely low as a result. Using Ergun's work on the effect of porosity on permeability for the aligned cylinder structure of the carbon nanotubes (see, S. Ergun, *Chemical Engineering Progress*, 1952; 48 (2); 90-98, which is incorporated by reference in its entirety), it is possible to model the significant non-linear increase in permeability at very large (>80%) porosity levels, thus making highly porous designs even more efficient in terms of Darcy drag reduction. The ultra-porous VACNT microfluidic features are therefore unique in that they provide both small feature diameters (~8 nm) and high porosity (>99%) and permeability (measured permeability values comparable to that of micro-/macroscopic porous elements), hence yielding unprecedented fluid accessibility into the nanoporous elements.

Figure 3:
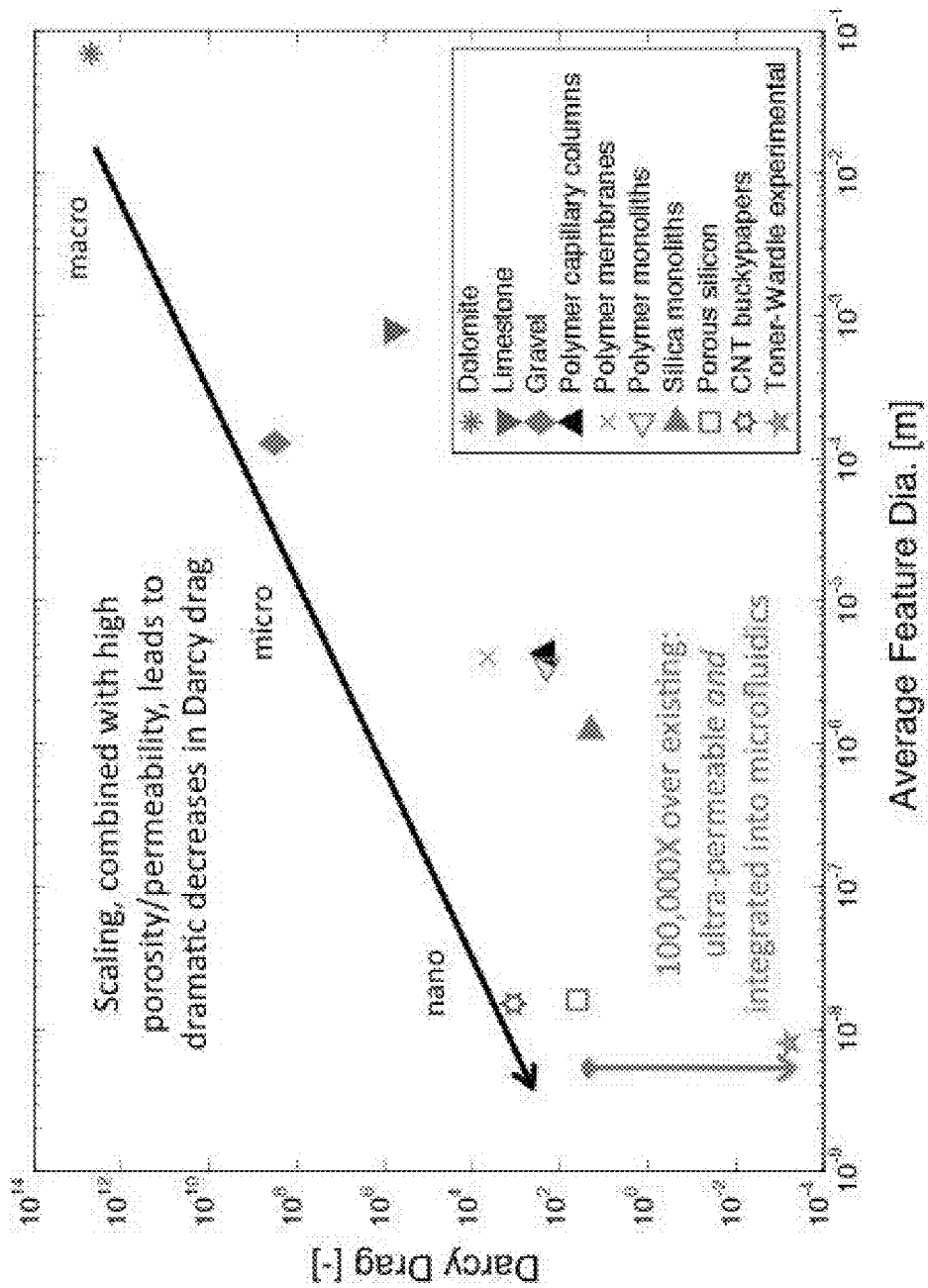
FIG. 3 is a graph depicting Toner-Wardle's ultra-high permeability microfluidic platforms are uniquely highly accessible to fluids.

The attractiveness of VACNT microfluidic features is evident in FIG. 3, where we compare the experimental Darcy drag of several macro- to nano-scale elements. Notably, Toner-Wardle's ultra-porous VACNT features yield Darcy drag 4-5 orders of magnitude lower than any other porous material. Noteworthy is also the large difference in Darcy drag between the VACNT elements and other nanoscale materials such as carbon nanotube buckypapers and porous silicon. Furthermore, bulk elements of these unique UPH features have been successfully integrated with shape-control into microfluidics.

Figure 4:
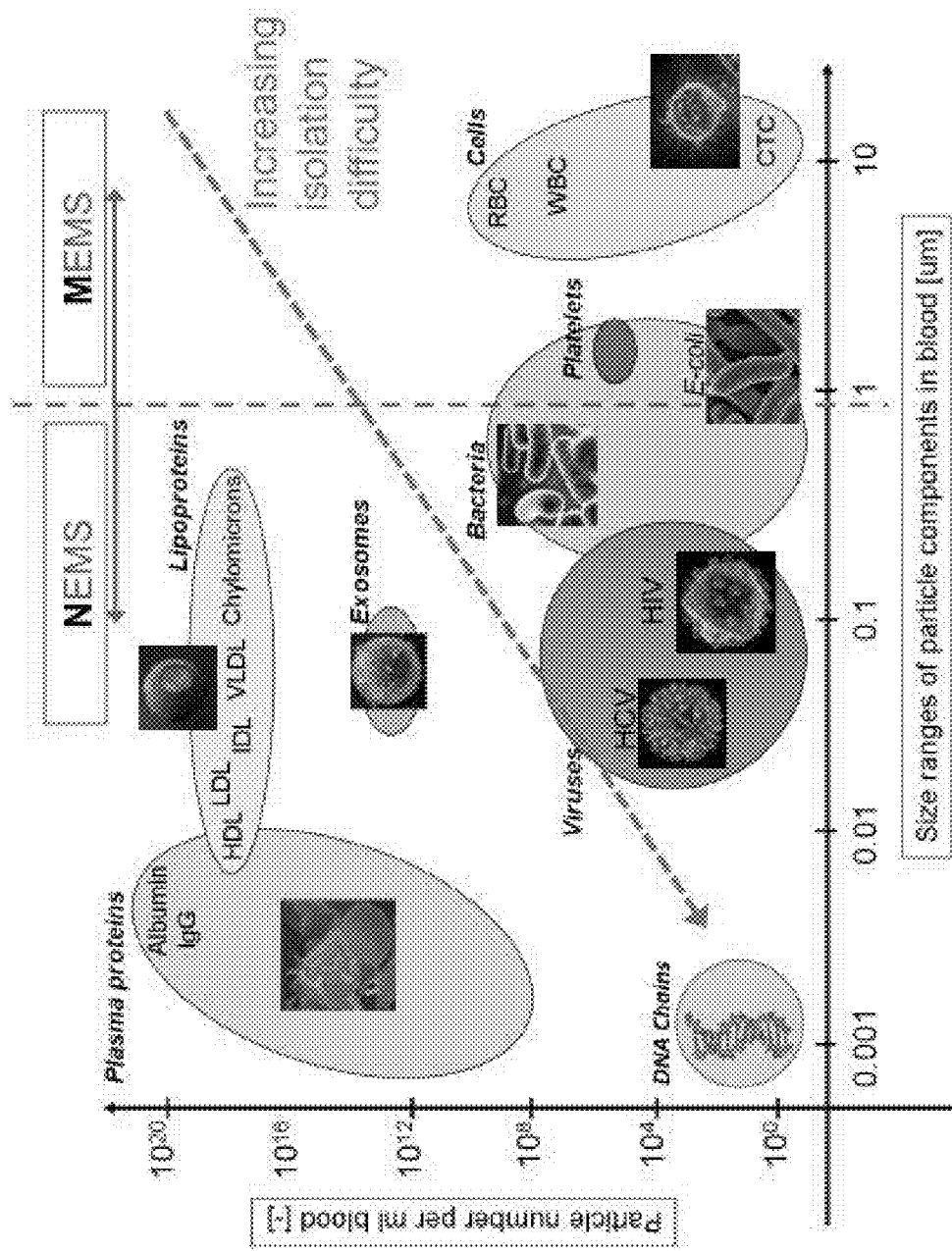
FIG. 4 is a graph depicting size and quantity distribution of particles carrying disease information in blood.

The application to be used as a vehicle for demonstrating the unique capability put forth is an LBL-enabled bioNEMS device for capturing HIV (lengthscale ~100 nm) which extends the level of difficulty from mm's (current work) to ~100 nm size particles that are at low quantities in blood (FIG. 4). Currently only cells are accessed in a meaningful way via bioMEMS and microfluidics, leaving the bioNEMS area open for development using the UHP nanoporous elements enhanced with LBL. HIV is chosen for device demonstration because it is a size challenge below cells.

The global health impact of an HIV diagnostic chip is enormous. The chip platform is cost effective as the carbon nanotube forests are not costly to fabricate despite the current market for carbon nanotube s, in fact much less so than etching Si. Furthermore, the rest of the chip is plastic. What is exciting about such demonstrations is the ability to probe bioparticles of nm-scale lengthscales via LBL-enabled nanoporous bioMEMS, a capability that has not yet been demonstrated. Cancer and other diseases generate small particles in blood and other fluids that has rich information that can be used to treat the disease. The nanoporous device elements will help the world capture the emerging richness of this data and understanding.

Figure 5:
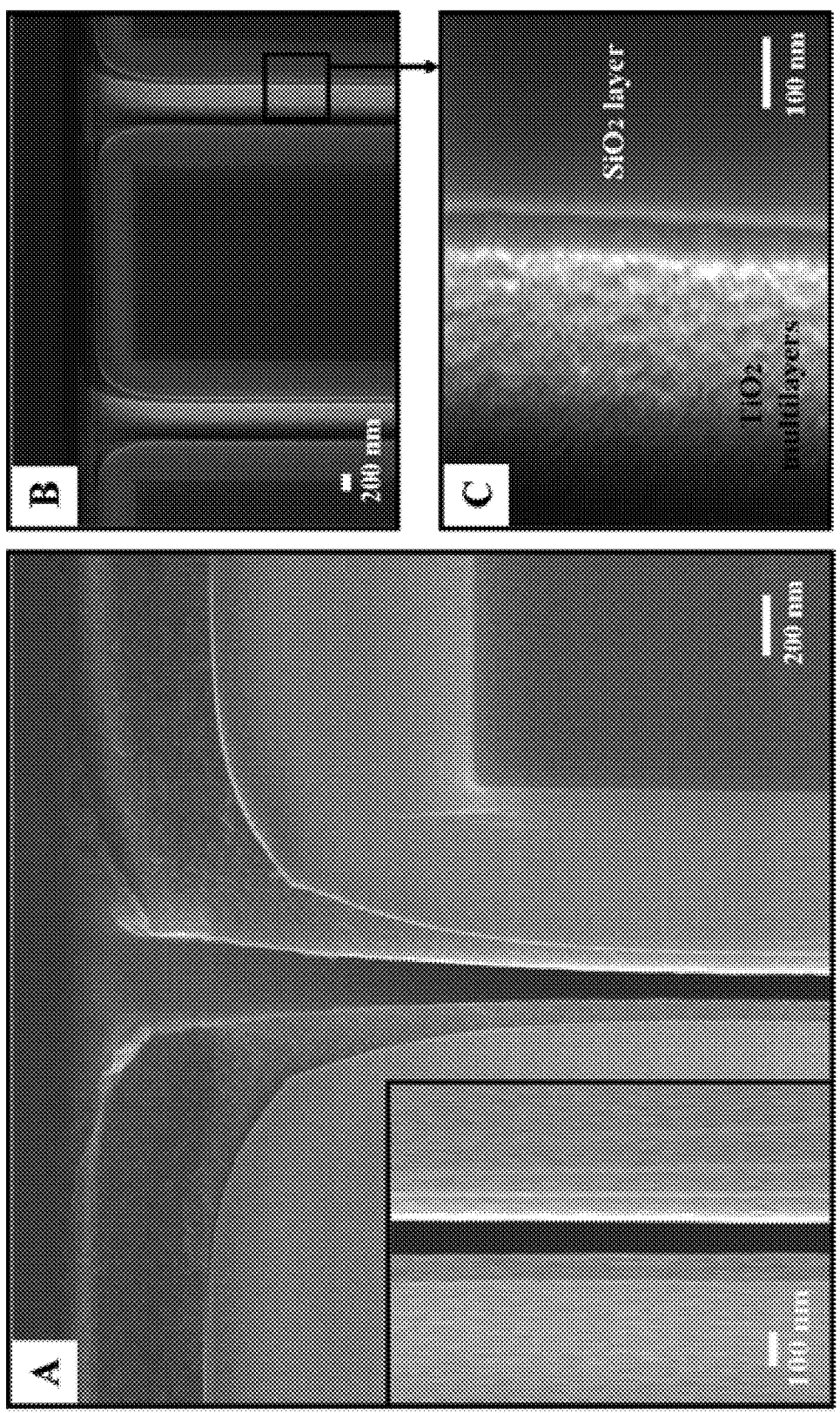
FIG. 5A-C are micrographs depicting layer-by-layer results under nanoscale constraint and range of layers and resulting layered materials possible.
FIG. 5D is a micrograph depicting micron-deep nanochannels systematically and conformally coated with layer-by-layer assembled materials including polymer/polymer, polymer/nanoparticle and nanoparticle/nanoparticle combinations.
Figure 5D:
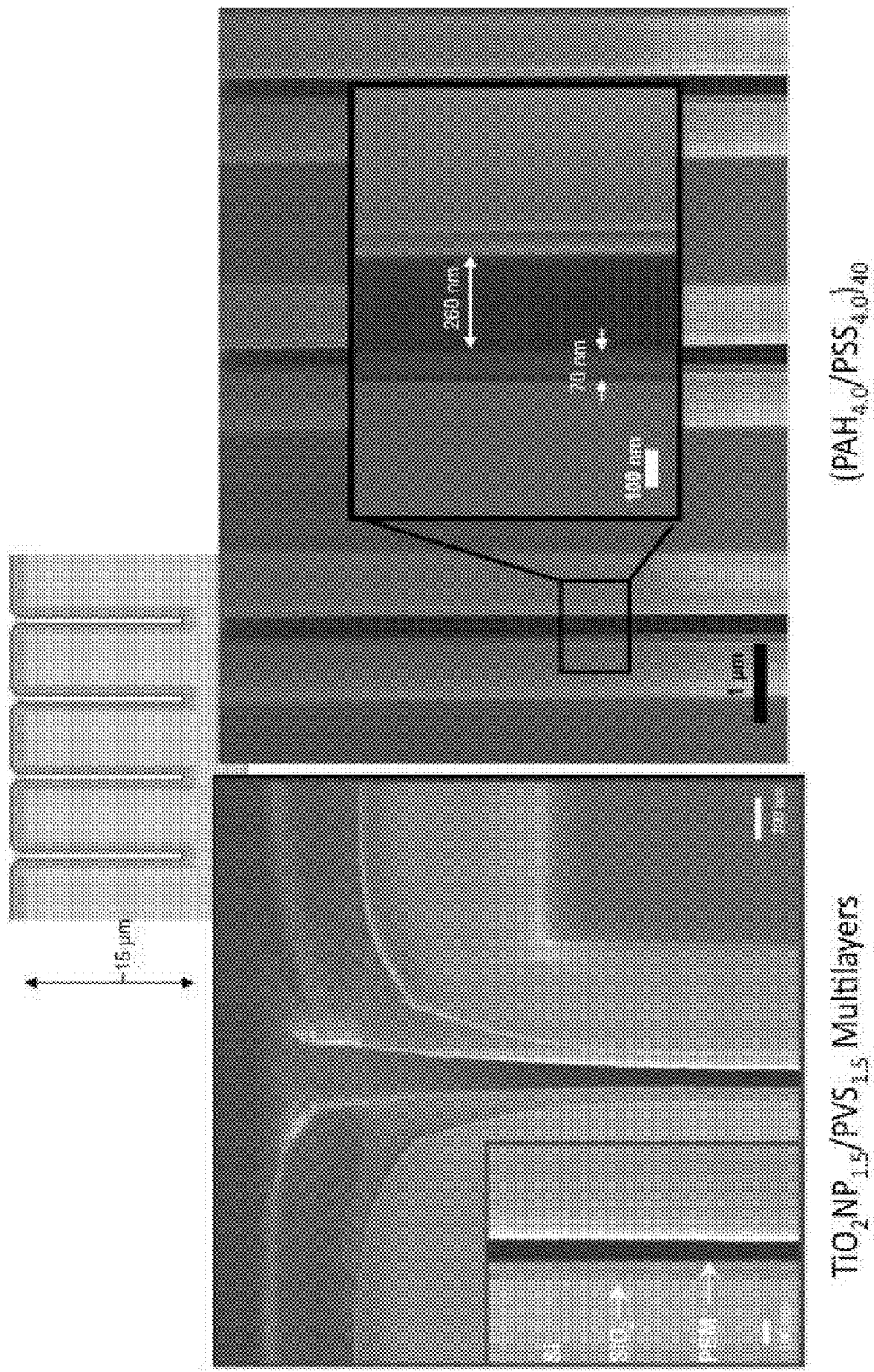

FIG. 5 demonstrates that micron-deep nanochannels can be systematically and conformally coated with LBL assembled materials including polymer/polymer, polymer/nanoparticle and nanoparticle/nanoparticle combinations. The wide-ranging functionality of these different materials makes it possible to tailor, at the nanoscale, physical properties including the mechanical, electrical and optical properties of the coatings as well as the chemical functionality of the coatings. In the latter case, functionalization of reactive groups within and at the surface of the multilayer coatings can be used to immobilize bioactive molecules including adhesion tripeptides, antibodies, enzymes and DNA. Control over the wet-state modulus of the coating further provides the ability to create non-fouling, non-adhesive surfaces that are able to prevent non-specific interactions with biological materials. Stimuli responsive LBL systems that significantly change their mechanical properties and dimensions with change in temperature and/or pH has been demonstrated. Amazingly, these diverse, functional multilayer systems can be LBL assembled onto surfaces within nanochannels with pore dimensions approaching the size of the assembling polymer or nanoparticle.

Figure 6:
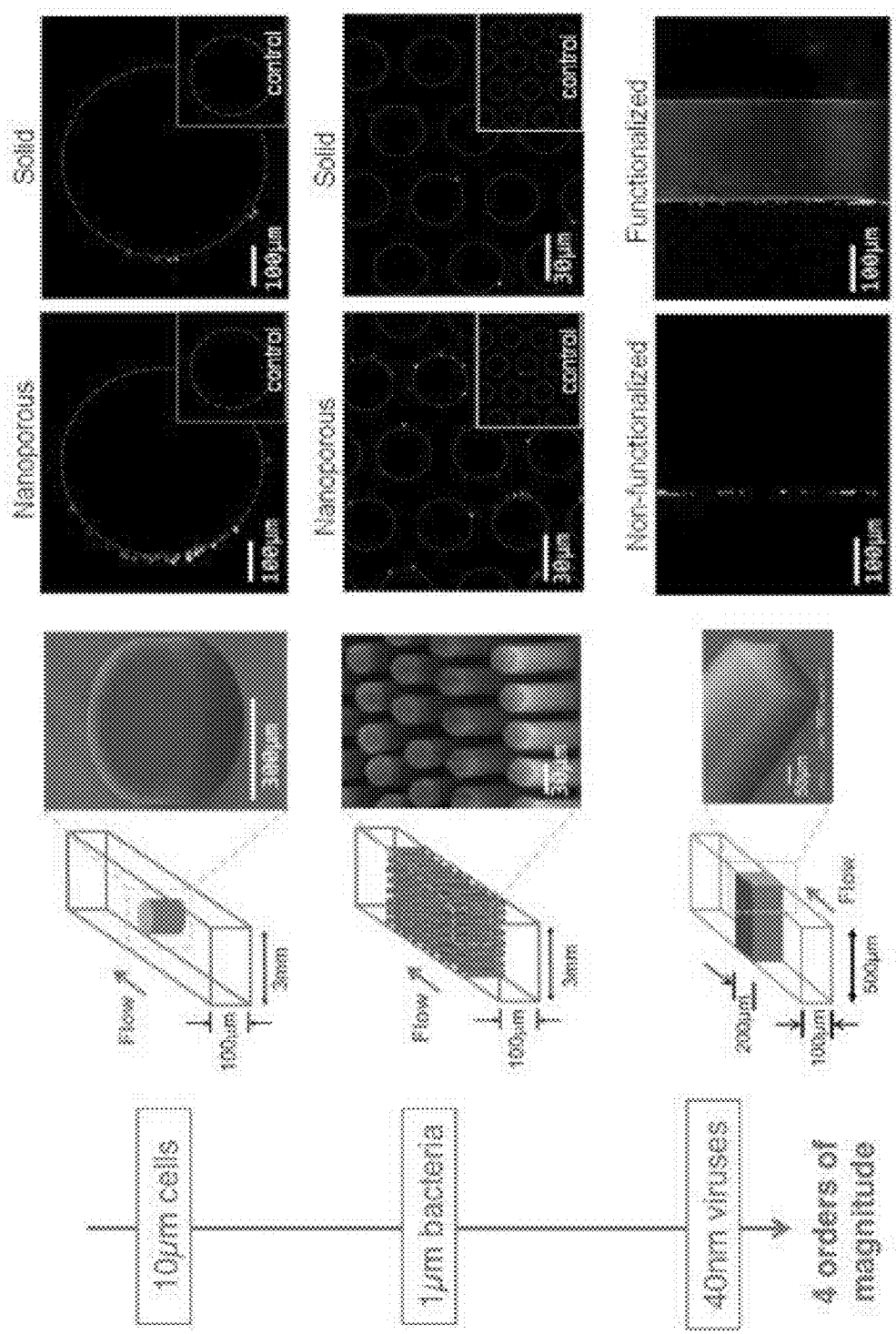
FIG. 6 depicts a nanoporous device operation allowing a variety of bioparticle lengthscales and chemical states to be manipulated, down into the nm-range, using both physical and affinity-based mechanisms.

FIG. 6 shows nanoporous device operation demonstrated to date allowing a variety of bioparticle lengthscales and chemical states to be manipulated, down into the nm-range, using both physical and affinity-based mechanisms.

Figure 8:
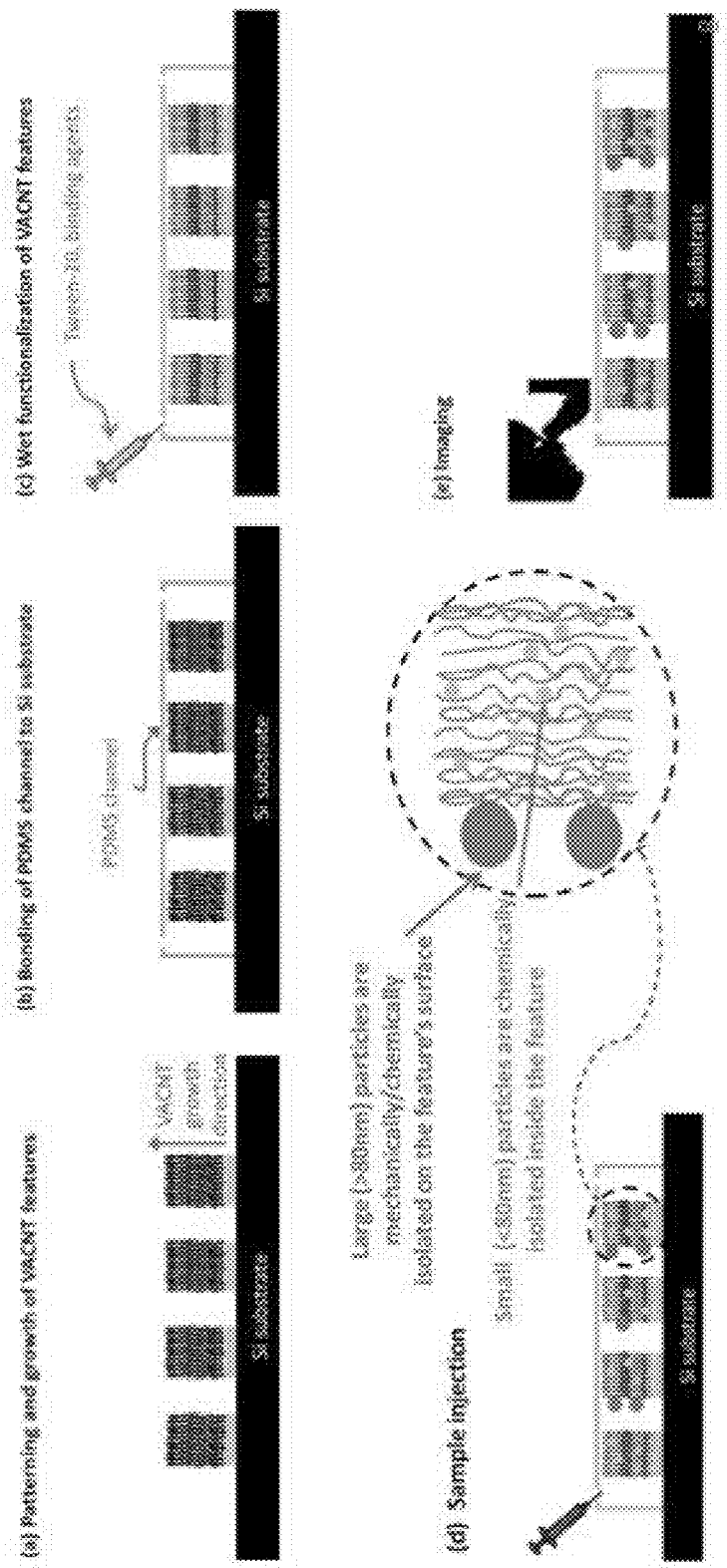
FIG. 8 is a schematic depicting overview of nanoporous element integration in microfluidic devices.

Toner-Wardle pioneered the introduction of ultra-high permeability elements in biomedical microfluidic devices. See, F. Fachin, G. D. Chen, M. Toner, and B. L. Wardle, *Proceedings of IEEE Sensors* 2010, 47-51, 2010, which is incorporated by reference in its entirety. Prior to their bioNEMS work, application of carbon nanotubes in biomedical applications was limited to dispersed, randomly-oriented carbon nanotubes utilized for biological imaging techniques (optical tags), electrical label-free bio-species detection, or CNT-mediated delivery of drugs and small-particles. See, Jingyi Chen, Shuyi Chen, Xianrui Zhao, Larisa V. Kuznetsova, Stanislaus S. Wong, Iwao Ojima, *Journal of the American Chemical Society* 2008 130 (49), 16778-16785, Nadine Wong Shi Kam, Theodore C. Jessop, Paul A. Wender, and, Hongjie Dai, *Journal of the American Chemical Society* 2004 126 (22), 6850-6851, and Zhuang Liu, Scott Tabakman, Kevin Welsher and Hongjie Dai, *Nano Research* 2 (2), 85-120, 2009, each of which is incorporated by reference in its entirety. These approaches were however unable to take advantage of the unique properties of carbon nanotube forests (e.g., morphology, tailorability, aspect ratio), thus being limited solely to chemical carbon nanotube-biospecies interactions. Toner-Wardle's work is the first integration of VACNTs in microfluidic devices without loss of structural properties or functionality. The microfluidic integration process (see also FIG. 8), which includes wet functionalization steps, preserves structural geometry up to 99% (or the original outer geometry) even under flow-through conditions. This is surprising because capillary forces do not deform/collapse the nanoporous elements as reported in the literature (see, D. N. Futaba, K. Hata, T. Yamada, T. Hiraoka, Y. Hayamizu, Y. Kakudate, O. Tanaike, H. Hatori, M. Yumura, S. Iijima, *Nat. Mater.* 2006, 5, 987, and De Volder, S. Tawfick, S. J. Park, D. Copic, Z. Zhao, W. Lu, A. J. Hart. Diverse 3D microarchitectures made by capillary forming of carbon nanotubes. *Advanced Materials*. 22:4384-4389, 2010, each of which is incorporated by reference in its entirety). It has been found to be the case in the devices across many types of nanoporous element features (e.g., see FIG. 6). Microfluidic compatibility results in the possibility to utilize VACNT elements to perform both multi-physics and multiscale bioparticle isolation on a single chip (see also FIG. 2): particles smaller than the average intra-carbon nanotube spacing (~80 nm in the baseline process) can penetrate the VACNT features and can be isolated using chemical-affinity, while larger particles that cannot penetrate the forest are isolated on the features' surfaces either via mechanical filtration or via chemical biorecognition. Preliminary work (see FIG. 6) shows isolation of bioparticles over four orders of magnitude in size—from cells to viruses—using 3 different feature and device geometries (i.e., single VACNT pillar, arrays of pillars, and rectangular filter).

1. LBL Palette and Formation with Nm-Scale Constraint

The broad palette of LBL-deposited materials developed by Cohen-Rubner is investigated for limitations within the ultra-high permeability nanoporous elements. Given the self-terminating nature of the LBL chemistries, numerous layers may be deposited within the nanopores while still maintaining high permeability. New ideas in this area include the ability to tailor LBL layers in the thickness direction of the features (by layering the fluids), in the direction of flow (in-plane of the devices for example) by depletion of the precursor molecules, and from element to element (e.g., different posts on a chip having different functionalities) via patterning and leveraging microfluidics for deposition. Multilayer coatings prevent non-specific binding of proteins and cells, functionalized to allow capture of specific targets such as DNA, antigens, immune cells, etc. For example, multilayers from polysaccharides like hyaluronic acid and chitosan prevent non-specific target capture and promote specific interactions with cells via, for example, CD44 receptor interactions Stimuli responsive multilayer coatings change physical and chemical properties in response to changes in solution temperature and/or pH and ionic strength.

2. Nanoporosity Tailoring

The microfluidic performance of VACNT elements is directly dependent on the forests' structural properties. Structural porosity is especially relevant as it largely determines the permeability, Darcy drag, and isolation efficiency of any VACNT feature. In order to tailor the nanoporosity of their VACNT structures, two different methods have been identified to control the average intra-CNT spacing and tube diameter of their forests.

Figure 7:
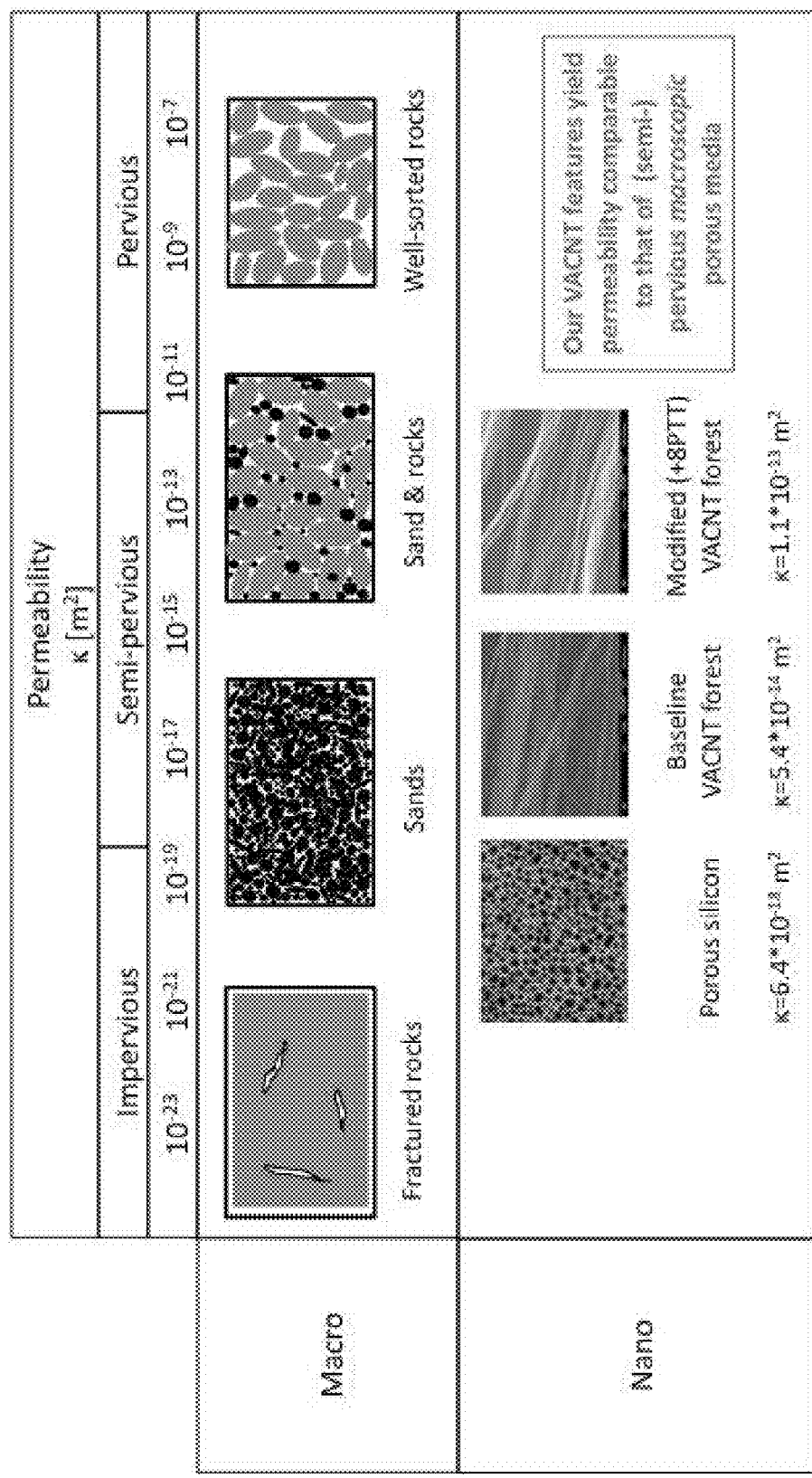
FIG. 7 is an example tailoring of nanoporosity.

The first method is based on fine tuning catalyst thickness and CNT growth conditions to modify both the average CNT diameter and the intra-CNT spacing. See, Gilbert D. Nessim, A. John Hart, Jin S. Kim, Donatello Acquaviva, Jihun Oh, Caitlin D. Morgan, Matteo Seita, Jeffrey S. Leib, Carl V. Thompson, *Nano Letters* 2008 8 (11), 3587-3593, which is incorporated by reference in its entirety. This solution can be used to increase forest porosity by, for example, increasing the intra-CNT spacing, thus also enhancing the forest's permeability. FIG. 7 indicates order of magnitude changes in permeability.

Conversely, the second method is based on forest mechanical densification to reduce intra-carbon nanotube spacing. See, Wardle, B. L., Saito, Diego S., Garcia, E. J., Hart, A. J., Guzman de Villoria, R., and Verploegen, E. A., *Advanced Materials*, Vol. 20, Issue 14, pp. 2655-2796, 2008, which is incorporated by reference in its entirety. This approach decreases permeability, but it allows targeting of even smaller particles. This method could for example be used to create forests with intra-carbon nanotube spacing ranging between 5-100 nm for isolation of particles such as very small viruses and proteins (see also FIG. 4). In general, the space between the two adjacent nanostructures is less than 100 nm, less than 90 nm, less than 80 nm, less than 70 nm, less than 60 nm, less than 50 nm, less than 40 nm, less than 30 nm, less than 20 nm, or less than 10 nm.

Both methods can be used to optimize bioNEMS devices for isolation and manipulation of both large and small bioparticles, particularly focusing on the simultaneous multiscale capabilities of this technology. Of course, selectively building up layers via LBL is also a way to reduce inter-carbon nanotube spacing in the forests, but this is separate from changing the porosity of the CNT scaffold itself.

3. LBL-Enabled BioNEMS HIV Device

Figure 9:
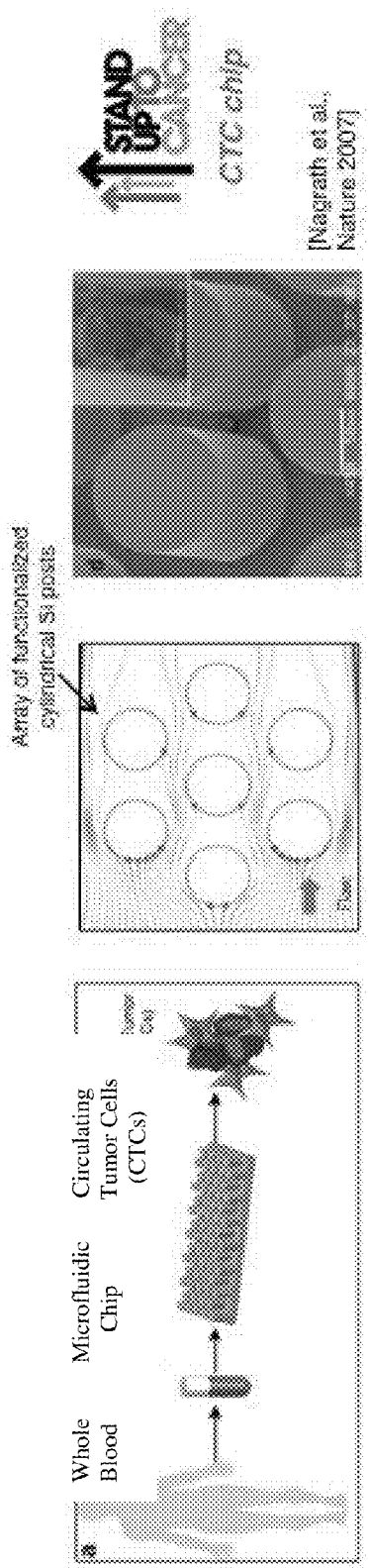
FIG. 9 is a diagram depicting global health impact: commercialization path of Toner's CTC chip that can be followed for other microfluidic chip assays enabled by the nanoporous elements enhanced with LBL, such as HIV isolation.

An LBL-enabled lab-on-a-chip platform for specific capture of viral particles, with particular focus on the Human Immunodeficiency Virus (HIV) is undertaken, including device-level design and testing. This work will follow the current overall device integration work (FIG. 8) that currently focuses on cancer cells, including model-based design of optimal nanoporous element geometries such as hollow features/elements which yields micro-nanoscale hybrid 'effective permeabilities'. Current state-of-the-art HIV diagnostic platforms are very limited, as they encounter significant difficulties in accessing a particle whose average diameter is 100 nm and whose clinically relevant concentration is ~100 virions per milliliter of plasma (concentration varies significantly depending on disease course). To date, the only widely used commercial method for measuring such low concentrations of virus requires nucleic acid amplification (e.g., qRT-PCR, quantitative reverse transcriptase polymerase chain reaction). These systems require high-end laboratory equipment, skilled technicians, and infrastructure for transportation of samples and communication of results. Due to a lack of some or all of these components, these viral test technologies are currently available to fewer than 10% of HIV patients worldwide. Reducing viral load tests to a low cost lab-on-a-chip platform would have a wide-reaching impact on global HIV care. The chip development can follow the recent deployment of Toner's $2^{nd}$-generation CTC chip (FIG. 9). New device-level ideas include using standard microfluidics concepts to create functionalized ultra-high permeability elements that have different functionalities, e.g., different posts on a chip have different functionalities. An extension of this idea is the possibility of creating chromatographic-functionalities via gradients in either LBL and/or porosity.

Figure 10A:
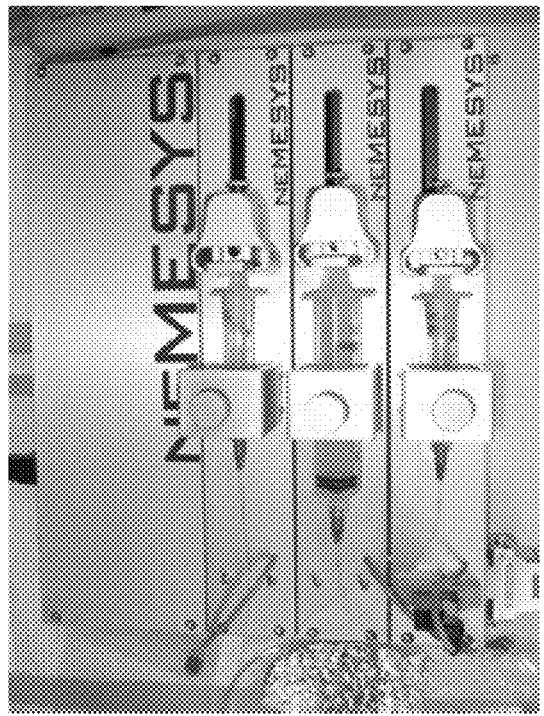
FIG. 10A is a schematic depicting integrated automated LBL depositions into microfluidics with nanoporous elements.
Figure 10B:
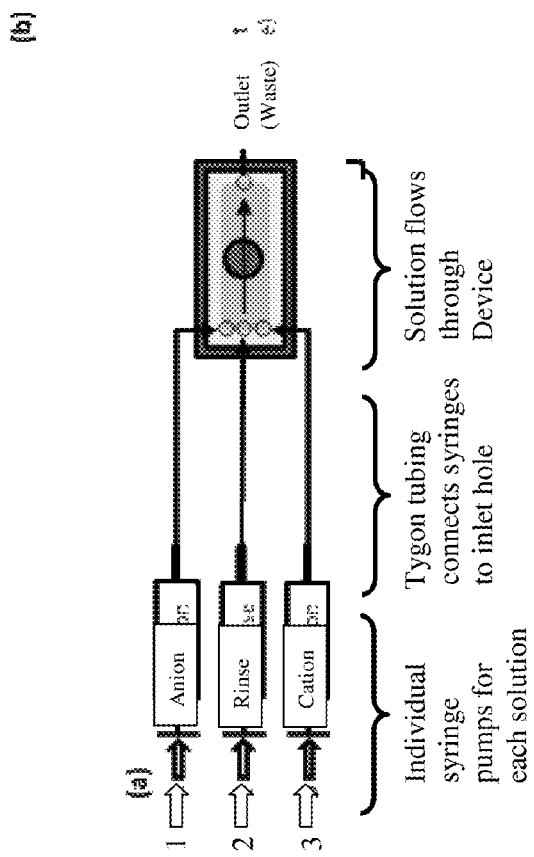
FIG. 10B is a photograph depicting integrated automated LBL depositions into microfluidics with nanoporous elements.
Figure 10C:
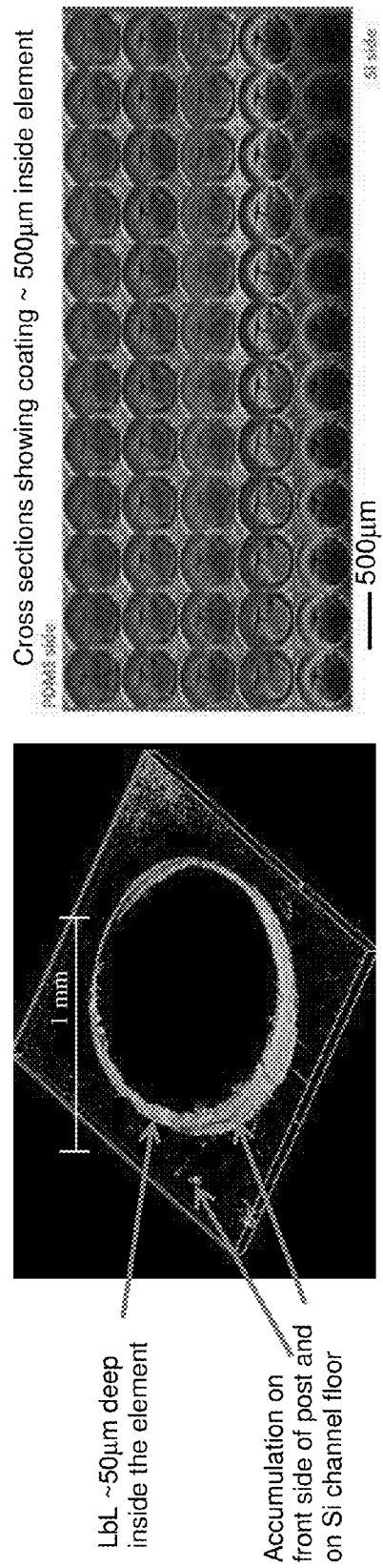
FIG. 10C is photographs depicting LBL depositions demonstrated inside microscopic nanoporous elements.

FIGS. 10A-10B shows integrated automated LBL depositions into microfluidics with nanoporous elements. FIG. 10C shows LBL depositions demonstrated inside microscopic nanoporous elements.

The UHP bioNEMS devices used to target additional information-carrying bioparticles in blood (left-hand side of FIG. 4) can be straightforwardly translatable to other biofluids such as sputum and urine for similar diagnostic purposes. Beyond bioNEMS, there are several applications, including energy storage and conversion materials (e.g., doping carbon aerogels takes hours due to their poor permeability, but the UHP VACNT elements with LBL could be tailored much more quickly to create Li-ion battery components. See, B. Dunn, J. W. Long, and D. R. Rolison, "Rethinking Multifunction in Three Dimensions for Miniaturizing Electrical Energy Storage", *The Electrochemical Society Interface*, Fall 2008, pp. 49-53, which is incorporated by reference in its entirety), lightweight 3D hierarchical composites, and sensors mimicking taste and smell (see, for example, M. A. Ryan, A. V. Shevade, C. J. Taylor, M. L. Homer, A. D. Jewell, A. Kisor, K. S. Manatt, and S. P. S. Yen, M. Blanco and W. A. Goddard, III, "Expanding the Capabilities of the JPL Electronic Nose for an International Space Station Technology Demonstration", AIAA paper #2006-01-2179, which is incorporated by reference in its entirety). Taste and smell sensors particularly benefit from high flows through the LBL-enabled ultra-high permeability elements. The future for such sensors is as embedded wireless sensing systems for real-time monitoring, such as sensors for both resource-rich (realtime monitoring of treatment) and resource-poor (lowcost/lowequip) diagnostic devices following CTC chip path. Beyond these additional applications for HDnanomaterials is the opportunity to develop sensors and additional functionalities by utilizing properties of the aligned CNTs themselves (UV, microwave, thermal and electrical transport, optical absorption), e.g., captured DNA from plasma could be 'released' by local microwave heating of the CNT forests to denature the captured DNA strands.

Figure 13:
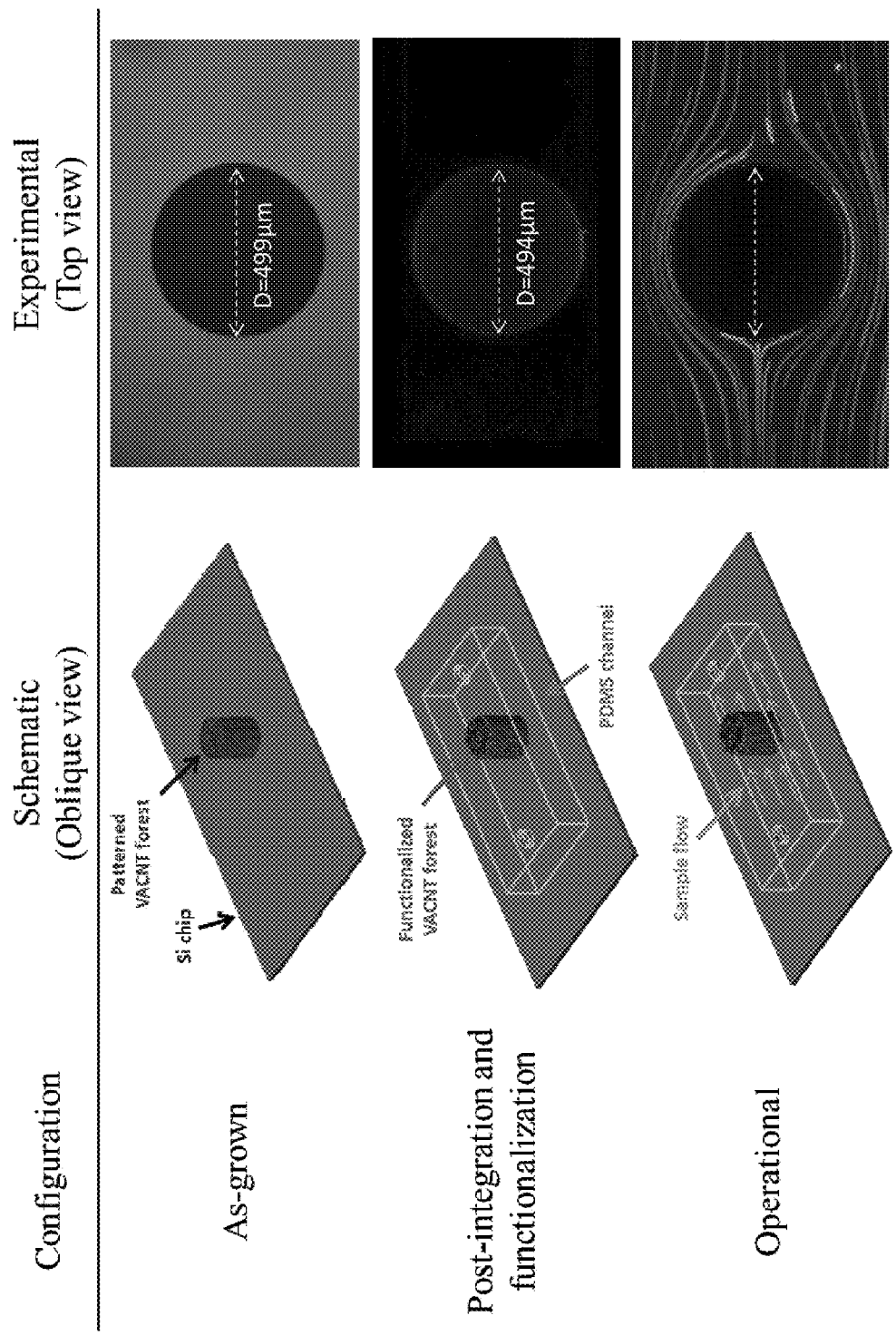
FIG. 13 is a series of schematic and experimental images of microfluidic integration of VACNT forests.

FIG. 13 shows a microfluidic integration of VACNT forests.

Other embodiments are within the scope of the following claims.

What is claimed is:

1. A fluidic device for manipulating particles comprising:
   a substrate that defines a fluid path; and
   one or more obstacles, each obstacle comprising a plurality of aligned nanostructures, wherein the nanostructures are coated with one or more layers of a plurality of nanoparticles and a plurality of polymer layers, wherein nanostructures form an outer surface of an obstacle in the fluid path; wherein the one or more obstacles are fixedly arranged within the fluid path such that some expected paths within the fluid path pass around the outer surface of an obstacle and some expected paths within the fluid path pass through the outer surface of an obstacle and into a network of spaces within the obstacle between the nanostructures.

2. The fluidic device of claim 1, wherein the nanostructures include a plurality of nanoparticles.

3. The fluidic device of claim 1, wherein the nanostructures include a plurality of polymer layers.

4. The fluidic device of claim 1, wherein a distance between adjacent nanostructures is less than 100 nm.

5. The fluidic device of claim 1, wherein a distance between adjacent nanostructures is less than 10 nm.

6. The fluidic device of claim 1, wherein the nanostructure is a carbon nanotube.

* * * * *